United States Patent [19]

Sanders et al.

[11] 4,348,509

[45] Sep. 7, 1982

[54] ALKOXYALKANOIC ACID PREPARATION

[75] Inventors: Andrea Sanders, Katy, Tex.; Leo Kim, Modesto, Calif.

[73] Assignee: Shell Oil Company, Houston, Tex.

[21] Appl. No.: 280,737

[22] Filed: Jul. 6, 1981

[51] Int. Cl.$^3$ .................................... C07C 51/235
[52] U.S. Cl. ............................................. 562/538
[58] Field of Search ................................ 562/538

[56] References Cited

U.S. PATENT DOCUMENTS 3,799,977  3/1974  Rutledge ..................... 562/538
4,256,916  3/1981  Morris et al. .................. 562/538

FOREIGN PATENT DOCUMENTS 747424  11/1966  Canada ........................ 562/538

*Primary Examiner*—Paul J. Killos

[57] ABSTRACT

Alkoxyalkanols are oxidized to the corresponding alkoxyalkanoic acids by contacting the alkanols with oxygen in the presence of a catalyst comprising platinum supported on a macroreticular cross-linked polystyrene/divinylbenzene resin. Enhanced rates are obtained.

7 Claims, No Drawings

ALKOXYALKANOIC ACID PREPARATION

BACKGROUND OF THE INVENTION

1. Field of the Invention

This invention relates to the production of alkoxyalkanoic acids by the oxidation of the corresponding alcohols using a catalyst comprising platinum supported on a macroreticular, cross-linked polystyrene resin.

2. Background

Alkoxyalkanoic acids find use as anionic detergents. These acids being composed of only the elements C, H and O do not pose the environmental problems that other detergents containing heteroatoms such as N, S, and P pose. Commercially, the alkoxyalkanoic acids are prepared in a two-step process of first reacting an alkoxyalkanol with sodium and then reacting the resultant ethoxide with the sodium salt of chloracetic acid. A one-step process avoiding the use of chloracetic acid and providing a NaCl free product would be of significant commercial interest.

U.S. Pat. No. 3,342,858, issued Sept. 19, 1967, generally discloses the use of supported platinum catalysts to oxidize alkoxyalkanoic to the acids. This process, however, is carried out in the presence of excess base. The presence of added base creates problems of excess by-product make and product purification. A commercial process avoiding the addition of base is highly desirable.

U.S. Pat. No. 3,929,873, issued Dec. 30, 1975 discloses a process for converting polyethylene glycols to dicarboxylic acids using a platinum on carbon catalyst.

SUMMARY OF THE INVENTION

This invention relates to a low temperature oxidative process for converting alkoxyalkanols to alkoxyalkanoic acids by reacting the alcohols with oxygen in the presence of a catalyst comprising platinum supported on a macroreticular cross-linked polystyrene resin having a surface area of 100–900 m$^2$g. The use of the instant catalyst provides enhanced reaction rates over the use of a conventional platinum on carbon catalyst, thus providing the instant process with a significant commercial advantage over prior art catalyst. The instant process also minimizes degradation products and provides for ease of product purification by avoiding the use of base in the reaction. The process is particularly suited to detergent range ethoxylate alcohols.

DESCRIPTION OF THE PREFERRED EMBODIMENTS

The present process converts alkoxyalkanols of the formula:

RO(CH$_2$CH R'O)$_n$CH$_2$CH$_2$OH wherein R is an alkyl group, preferably of 1 to about 22; more preferably of about 11 to about 18 carbon atoms, R' is hydrogen or methyl or mixtures thereof (on the individual molecule) and n is an integer of from 1 to about 12, preferably of from about 2 to about 9, to the corresponding alkoxyalkanoic acids of the formula:

RO(CH$_2$CH R'O)$_n$CH$_2$CO$_2$H by reacting the alcohols with oxygen in the presence of a catalyst comprising platinum metal supported on a macroreticular, cross-linked polystyrene resin. The R group can be substituted with any substituent which does not interfere with the oxidation of the hydroxy group. Such substituents include —R", —CH$_3$, —COOH, —CONH$_2$ and —COOR" wherein R" is an alkyl or aryl group. The process is particularly suited to detergent range ethoxylated, or propoxylated alcohols with alkyl chains (R) of about 8 to about 20, preferably about 11 to about 18. The R' group on an individual molecule can be hydrogen, methyl or mixtures thereof. For example, straight ethoxylates, straight propoxylates and mixed ethoxylate-propoxylate detergent alcohols are commercially available. The number of such alkoxyate groups, (CH$_2$CH R'O), range from 1 to about 12. Commercially, detergent range ethoxylate alcohols are available with an average of 3, 7, 9 and 12 ethoxylate units per molecule. Others can readily be prepared.

The support used to prepare the catalyst of the instant invention is a macroreticular cross-linked polystyrene/divinylbenzene polymer. These resins differ from the traditional ion exchange resins in that they have no functional groups incorporated into the resin structure. These resins are typically prepared by the co-polymerization of styrene and divinylbenzene. Porosity and surface areas are controlled by regulating the concentration of divinylbenzene. These resins are available in a wide range of surface areas, ranging from about 100 to about 900 m$^2$/g. The preferred resins have a surface area ranging from about 700 to about 900 m$^2$/gm, a porosity ranging from about 40 to about 60 ml (ml of resin) and an average pore diameter ranging from about 40 to about 60 angstroms. A typical and preferred resin is that supplied by Rohm & Haas Company and known as AMBERLITE®XAD-4. It has a surface area of about 750 m$^2$/gm, a porosity of about 0.50–0.55 ml of pore/ml of resin and an average pore diameter of about 50 angstroms. Similar materials are the commercially available Bio-Beads S series supplied by BIO-RAD Laboratories.

The catalysts are typically prepared by impregnating the resin with an aqueous solution of a platinum salt such as H$_2$PtCl$_6$ or K$_2$PtCl$_4$, drying the impregnated resin, reducing the impregnated resin in hydrogen followed by washing with water to remove excess ions. The catalysts are typically reduced in hydrogen at about 75°–150° C. An additional reduction with metal hydroides such as NaBH$_4$ or LiAlH$_4$ in order to assure complete reduction of the platinum salt is useful. The amount of platinum metal supported on the resin is not critical. From about 1–20, preferably 5–15 percent by weight of platinum on the support is satisfactory and provides an economical use of platinum.

The reaction is conducted under relatively mild conditions with good results being obtained using a temperature of about 50°–110° C., preferably from about 60°–100° C. Pressures of from about atmospheric up to about 1500 psig can be employed with good results. Higher temperatures and the use of high molecular weight reactants such as detergent range ethoxylate alcohols, require the use of higher pressures.

The reaction may be carried out in an inert solvent with the preferred solvent being water, although any solvent that is non-reactive and miscible with the reactant materials and reaction products may be used. Other suitable solvents include p-dioxane and tetrahydrofuran.

The oxidizing gas can be oxygen or an oxygen-containing gas such as air. Whereas pure oxygen can satisfactorily accomplish the desired conversion, dilution of the oxygen with an inert gas such as nitrogen, helium, argon $CO_2$, or other similar gas is preferred. No criticality is found in the concentration of oxygen in the oxidizing gas although practical considerations make concentrations less than 10% unattractive.

The reaction product can be purified by conventional means say by azeotropic distillation with benzene, etc., by fraction distillation, fractional crystallization, etc.

The process of this invention will be further described by the following illustrative embodiments which are provided for illustration and are not to be construed as limiting the invention.

ILLUSTRATIVE EMBODIMENTS

A. Catalyst Preparation

The following illustrates a typical method of preparing platinum catalysts supported on macroreticular cross-linked polystyrene resins.

Washing of the Resin

The resins are washed before impregnation by placing the resin in absolute methanol and stirring occasionally over a 20 min. period. The resin is filtered on a fritted glass funnel and washed with absolute methanol, 50% methanol in water, and water and then evacuated briefly to remove excess water, but not to dryness. The resin can then be stored in a clean glass jar for future use.

Impregnation

Chloroplatinic acid, $H_2PtCl_6$ (5.0 g.), is dissolved in 12 ml $H_2O$ and is used to impregnate two batches of 17 g each of XAD-4 (Rohm & Haas) resin (total of 34 g resin). The chloroplatinic acid solution (6 ml) is added dropwise to the resin (17 g) in a porcelain dish. A porcelain spatula is used to help coat the resin evenly and an air gun is used periodically to remove excess moisture. The impregnated catalyst is briefly dried with an air gun until it is free-flowing. The catalyst is transferred to a quartz calcining tube and drying in a furnace is carried out at 100°–120° C. with a nitrogen flow of 200 cc/min.

Reduction in Calcining Tube

After all of the $H_2O$ is removed by calcination, 100 cc/min $H_2$ is added to the 200 cc/min $N_2$ stream while keeping the furnace at 100°–120° C. The quartz tube is periodically inspected and the reduction is continued until the catalyst is completely black.

Reduction under Pressure

The catalyst is further reduced under $H_2$ pressure in an autoclave. The catalyst is transferred to an autoclave which is purged three times with $N_2$ and then pressured with $H_2$ to 750 psig. The autoclave is then heated at 100° C. for 1 hr.

Washing the Reduced Catalyst

Using a large fritted glass funnel, the catalyst is washed with copious amounts of distilled $H_2O$. The water washings are checked periodically for chloride ion with a $AgNO_3$ solution. When the washings are apparently free of chloride ions, the catalyst is washed with reagent grade acetone, followed by 50% acetone in $H_2O$, and finally $H_2O$. The catalyst is dried in the vacuum oven at 100° C. and 3 mm Hg for 1 hr. and then stored in a glass vial for future use.

$NaBH_4$ Treatment

Several catalysts are further treated with $NaBH_4$ before drying as above. The washed Pt/XAD catalyst (11.0 g) is placed in 50 ml of $H_2O$ in a 500 ml 3-necked round bottom flask fitted with a dropping funnel, $N_2$ inlet with frit to bubble $N_2$ through the solution, and a $N_2$ outlet to a Nujol bubbler. $NaBH_4$ (2.0 g) is dissolved in 50 ml $H_2O$ and transferred to the dropping funnel. The system is purged with $N_2$ and the $NaBH_4$ solution is added dropwise over a 30 min. period. Hydrogen evolution will be noted. After the $NaBH_4$ addition is complete, the flask is swirled occasionally for 30 min. The catalyst is filtered and washed with 5 liters of $H_2O$ before drying in a vacuum oven at 100° C. and 3 mm Hg for 1 hr.

$LiAlH_4$ Treatment

Pt/XAD catalyst (6 g) is dried in a vacuum oven at 100° C. and 3 mm Hg for 1 hr. The catalyst is added to freshly distilled THF and kept under a nitrogen blanket. A solution of 0.5 g $LiAlH_4$ in 25 ml THF is added dropwise to the catalyst. After 30 min. water is cautiously added and then the catalyst is filtered and washed with copious amounts of water. The catalyst is then dried in a vacuum oven at 100° C. and 3 mm for 1 hr.

B. Process

Example 1

In a typical experiment about 5 grams of Pt/XAD-4 catalyst (~6% wt Pt on XAD-4 resin; 0.15 milligram equivalent weight (meq) of total platinum added) and 12 grams of Shell Neodol ® ethoxylate 23-3 (prepared by ethoxylating a $C_{12}$ and $C_{13}$ mixture of substantially straight chain alcohols ($C_{12}:C_{13} \sim 40:60$) to an ethoxylate alcohol having on the average about three ethylene oxide units per molecule) are charged to a glass-lined autoclave. The autoclave is pressured with 50 psig $N_2$ and 350 psig $H_2$ (room temperature measurement). The autoclave is heated to 80° C. and is run for 7.5 hours. The reactor is cooled and the product is analyzed. The rate of production of product acid is found to be about 6.7 meq of product acid per meq of platinum per hour.

Comparative Experiment

The above experiment is repeated using a commercial 10% platinum on carbon catalyst such as that supplied by Engelhard, lot G.3684 0.31 meq of total platinum added). The rate of production of product acid using the catalyst is only 4.8 meq of product acid per meq of platinum per hour.

EXAMPLE 2

Repeating the above experiment with about 10 grams of Pt/XAD-4 catalyst (0.32 meq of total platinum added) which had been additionally reduced with $NaBH_4$ as described in part A above and with 12 grams of Shell Neodol ® exthoxylate 23-3T(23-3 which has had the unreacted alcohols and lower exthoxylates topped off so that the final product has about five ethylene oxide units per molecule) results in a rate of production of product acid of 7.1 meg of product acid per meg of platinum per hour.

What is claimed is:

1. A process for preparing an alkoxyalkanoic acid of the formula:

$$RO(CH_2CHR'O)_n CH_2CO_2H$$

wherein R is an alkyl group of 1 to about 22 carbon atoms, R' is hydrogen or methyl or a mixture thereof (on the individual molecule) and n is an integer of from 1 to about 12 by reacting the corresponding alkoxyalkanol with oxygen at a temperature of from about 50° to about 110° C. in the presence of a catalyst comprising platinum supported on a macroreticular cross-linked polystyrene/divinylbenzene resin having a surface area ranging from about 700 to about 900 m$^2$/g.

2. The process of claim 1 wherein the temperature ranges from about 60° to about 100° C.

3. The process of claim 1 wherein the pressure ranges from about atmospheric to about 1500 psig.

4. The process of claims 1, 2 or 3 wherein R ranges from about 8 to about 20.

5. The process of claims 1, 2 or 3 wherein R range from about 11 to about 18.

6. The process of claims 1, 2 or 3 wherein the amount of platinum on the support ranges from about 1 to about 20 percent by weight of total catalyst.

7. The process of claim 1, 2 or 3 wherein the amount of platinum on the support ranges from about 5 to about 15 percent by weight of total catalyst.

* * * * *